United States Patent [19]

Darras

[11] Patent Number: 4,678,668

[45] Date of Patent: Jul. 7, 1987

[54] METHOD OF REDUCING SOFT TISSUE SWELLING AND PAIN

[75] Inventor: Robert L. Darras, San Pedro, Calif.

[73] Assignee: MD Associates, Rolling Hills Estates, Calif.

[21] Appl. No.: 792,001

[22] Filed: Oct. 28, 1985

[51] Int. Cl.⁴ .............................................. A61K 37/48
[52] U.S. Cl. ................................. 424/94.1; 424/94.2
[58] Field of Search ........................................... 424/94

[56] References Cited

U.S. PATENT DOCUMENTS 3,003,917  10/1961  Beiler et al. ............................ 167/73

OTHER PUBLICATIONS

Chem. Abst., 71-111 160n, (1969).
Chem. Abst., 72-119657w, (1970).
Chem. Abst., 78 70135g, (1973).

*Primary Examiner*—Stanley J. Friedman
*Attorney, Agent, or Firm*—Spensley Horn Jubas & Lubitz

[57] ABSTRACT

Disclosed is a composition and a method for reducing soft tissue swelling and pain. A composition comprising of proteolytic enzyme and a transfer vehicle is topically applied to the injured bodily area. Relief is rapid.

6 Claims, No Drawings

METHOD OF REDUCING SOFT TISSUE SWELLING AND PAIN

FIELD OF THE INVENTION

This invention relates to a composition and method for reducing soft tissue swelling and pain using topical application of a combination of a proteolytic enzyme and a transfer vehicle.

PRIOR ART

One of the most common medical afflictions effecting man is pain, tenderness and swelling of bodily regions. For example, pain, tenderness and swelling often accompanies contusions, sprains, ruptured superficial veins and tenosynovitis. While there are a variety of treatments for such pain, tenderness and swelling, there is still a great need for alternative methods and compositions for treating these aliments.

Proteolytic enzymes have been demonstrated to be effective therapeutics in reducing inflammation when administered orally, intramuscularly, intraperitonelly, and subcutaneously. For example, see U.S. Pat. No. 3,324,002 to Antonides, U.S. Pat. No. 3,003,917 to Beiler, U.S. Pat. No. 3,004,893 to Martin, and U.S. Pat. No. 3,224,942 to Martin. In such methods of administration, the proteolytic enzyme is typically highly concentrated. However, proteolytic enzymes have thus far not been administered topically in a transfer vehicle and in low concentration.

SUMMARY OF THE INVENTION

The present invention is directed to a composition and a method for reducing soft tissue swelling and pain in humans and animals by topically administering a therapeutic composition comprising a topically administrable transfer vehicle and a proteolytic enzyme. It is believed that the proteolytic enzyme breaks down some of the fibrinous membranes within the swollen bodily region and allows fluid to move through the soft tissue thereby alleviating soft tissue swelling, tenderness and pain. The transfer vehicle can comprise any substance which facilitates transport of the proteolytic enzyme through the skin into the soft tissue. The proteolytic enzyme is preferably purified papain.

DETAILED DESCRIPTION OF THE INVENTION

The following description is of the best presently contemplated mode of carrying out the invention. This description is made for the purpose of illustrating the general principles of the invention and is not to be taken in a limiting sense. The scope of the invention is best determined by reference to the appended claims.

The present invention is concerned with a composition and a method for reducing soft tissue swelling, tenderness and pain using topical application of a combination of a proteolytic enzyme, or any substance capable of dispersing fluid in soft tissues, with any transfer vehicle which can transport the active ingredients through the skin into the soft tissue. In particular, the composition of the present invention comprises a topically administerable pharmaceutical carrier and a proteolytic enzyme.

The proteolytic enzymes may be selected from the group consisting of papain, chymopapain, hyaluronidase, desoxyribonuclease, trypsin, chymotrypsin, bromelain and mixtures thereof. Preferably, papain is used.

The topically administerable pharmaceutical carrier or transfer vehicle may include any substance capable of transporting the active ingredients through the skin into the affected soft tissue area. The transfer vehicle thus may be glycerine, alcohol, hydroalcoholic or water based. Examples of vehicles include aloe vera which is gel base, or Vehicle/N which is a product of Neutrogena Corporation. For example, Vehicle/N contains 47.5% alcohol, 4% isopropyl alcohol, purified water, propylene glycol and laureth-4. Other alcohol, glycerine, hydroalcoholic or water based transfer vehicles and pharmaceutical carriers are within the scope of the present invention. See Table 1, supra.

The composition of the present invention is prepared by dissolving from 10 to 100 units of the proteolytic enzyme per 50 ml in the transfer vehicle, followed by shaking. Preferably, about 18 units of purified papain is dissolved in 50 ml of Vehicle/N. The resulting solution may be applied to the tender bodily region. For example, the papain solution may be applied topically by utilizing an applicator tip having a cloth-like membrane which fits on the top of a bottle of the solution and which allows the solution fluids to contact the skin. Such bottle and applicator tips are well known to those skilled in the art.

The following table includes examples of compositions of the present invention which are presented for illustrative purposes only.

TABLE 1

| | RANGE OF INGREDIENTS (parts per 100 by weight) | PREFERRED AMOUNT (parts per 100 by weight) |
|---|---|---|
| Ointment Base | | |
| Aquaphor[1] | 90 to 98 | 98 |
| Tween 80[2] | 0.5 to 3 | 0.5 |
| water, distilled | 1.0 to 5.5 | 1.0 |
| Papain[3], purified | 0.5 to 1.5 | 0.5 |
| Lotion | | |
| Glycerin | 47.75 to 49.25 | 49.25 |
| Tween 80 | 1.0 to 3.0 | 1.0 |
| water, distilled | 47.75 to 49.25 | 49.25 |
| Papain, purified | 0.5 to 1.5 | 0.5 |
| Solution | | |
| Vehicle/N | 98.5 to 99.85 | 99.5 |
| Papain, purified | 0.15 to 1.5 | 0.5 |
| Gel | | |
| Aloe-Water Gel | 98.5 to 99.85 | 99.5 |
| Papain, purified | 0.15 to 1.5 | 0.5 |

[1] Aquaphor is an ointment base sold under the trademark Aquaphor by Beiersdorf. It contains petrolatum, mineral oil, mineral wax and wool wax alcohol.
[2] Tween 80 is an ointment sold under the trademark Tween 80 by City Chemical. It contains polyoxethylene, sorbitan mono-oleate and olethytan.
[3] Papain is a purified product sold under the trademark Papain M-70 by Meer Corporation.

The following are examples of use of the composition and method of the present invention showing the utility of 18 units of purified papain in 50 ml of Vehicle/N.

CASE I

Patient—Age 48 yrs.

Pain and tenderness over the anterior ankle joint of four days duration. Pain at rest during the night severe enough to prevent sleep and with walking; tenderness without visible swelling over the tendon sheath of the fourth extensor tendon. X-ray of the ankle was normal. Application of topical medication produced almost instant relief. There has been no recurrence of symptoms. DIAGNOSIS: Teno-Synovitis.

CASE II:

Patient—Age 29 yrs.

Pain and swelling of the left index finger of two days duration. This female was bitten by her horse while wearing gloves which protected her from any significant penetration of the skin. The finger was swollen to approximately one and a half times normal size over its entire length. No clinical evidence of fracture or infection. Application of topical medication with reduction of swelling to normal size within ten minutes. No recurrence of swelling or pain. DIAGNOSIS: Contusion of finger.

CASE III:

Patient—Age 24 yrs.

Severe sprain of the right ankle, evening prior to visit. Severely swollen, tender lateral malleolar area, X-ray-no fracture. Application of topical medication over area of swelling and surrounding area with 80% reduction of swelling. Ankle taped. On follow-up swelling die not recur. DIAGNOSIS: Sprain of right ankle.

CASE IV:

Patient—Age 42 yrs.

Painful swelling of left upper calf started while playing tennis. Raised bluish area with burning sensation in area of swelling. Exam revealed rupture of superficial vein. Topical medication applied produced complete and immediate relief of pain and swelling. Discoloration remains. No recurrence. DIAGNOSIS: Ruptured superficial vein-left leg.

CASE V:

Patient—Age 41 yrs.

Pain in the anterior portion of the arch of left foot. Pain began while jogging and has become severe enough to keep patient awake at night. Hurts to walk. X-ray of the foot is negative for bone injury or disease. Application of topical medication with complete relief within five minutes. No recurrence. DIAGNOSIS: Sprain of left arch.

I claim:

1. A method for reducing soft tissue swelling and pain of animals comprising administering topically to the animal a composition comprising from 10 to 100 units of a proteolytic enzyme selected from the group consisting of papain, trypsin, chymotrypsin, hyalurionidase or mixtures thereof dissolved in a transfer vehicle in an amount sufficient to transport the proteolytic enzyme through the soft tissue of the animal.

2. A method according to claim 1 wherein the proteolytic enzyme is papain.

3. A method for reducing soft tissue swelling and pain of animals comprising administering topically to the animal 10 to 100 units of a composition comprising a proteolytic enzyme selected from the group consisting of papain, trypsin, chymotrypsin, hyalurionidase or mixtures thereof dissolved in a transfer vehicle in an amount sufficient to transport the proteolytic enzyme through the soft tissue of the animal, wherein the transfer vehicle is selected from the group consisting of glycerin, alcohol, water and hydroalcoholic based topically administerable pharmaceutical carriers.

4. A method according to claim 3 wherein the transfer vehicle is a mixture consisting essentially of alcohol, isopropyl alcohol, purified water, propylene glycol, and laureth-4.

5. A method according to claim 1 wherein from 10 to 100 units of proteolytic enzyme per 50 ml of liquid transfer vehicle are administered.

6. A method for reducing soft tissue swelling and pain in animals consisting essentially of topically administering to the soft tissue of the animals a solution consisting essentially of 18 units of papain per 50 ml of a mixture consisting essentially of alcohol, isopropyl, alcohol, purified water, propylene glycol, and laureth-4.

* * * * *